United States Patent
Hirakui et al.

(10) Patent No.: US 6,929,602 B2
(45) Date of Patent: Aug. 16, 2005

(54) ENDOSCOPE APPARATUS

(75) Inventors: Katsuya Hirakui, Ootawara (JP);
Akinori Shigihara, Ootawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 186 days.

(21) Appl. No.: 10/391,585

(22) Filed: Mar. 20, 2003

(65) Prior Publication Data
US 2003/0216617 A1 Nov. 20, 2003

Related U.S. Application Data

(63) Continuation-in-part of application No. 09/392,717, filed on Sep. 9, 1999, now abandoned.

(30) Foreign Application Priority Data

Sep. 28, 1998 (JP) .............................. 10-273703

(51) Int. Cl.[7] ................................ A61B 1/12
(52) U.S. Cl. .................. 600/159; 600/156; 600/103
(58) Field of Search ................ 600/103, 153, 600/156, 158, 159

(56) References Cited

U.S. PATENT DOCUMENTS

| | | |
|---|---|---|
| 4,982,726 A | 1/1991 | Taira |
| 5,053,002 A | 10/1991 | Barlow |
| 5,159,446 A | 10/1992 | Hibino et al. |
| 5,678,568 A | 10/1997 | Uchikubo et al. |
| 5,868,666 A | 2/1999 | Okada et al. |
| 5,894,322 A | 4/1999 | Hamano et al. |
| 6,095,971 A | 8/2000 | Takahashi |

FOREIGN PATENT DOCUMENTS

| | | |
|---|---|---|
| JP | 56-66232 | 6/1981 |
| JP | 1-297047 | 11/1989 |
| JP | 3-277340 | 12/1991 |
| JP | 2000-102506 | 4/2000 |

*Primary Examiner*—Beverly M. Flanagan
(74) *Attorney, Agent, or Firm*—Oblon, Spivak, McClelland, Maier & Neustadt, P.C.

(57) ABSTRACT

In an endoscope apparatus, an air/water switch (15) that is provided in an operating section (9) of an endoscope (5) each generate an air feed on/off signal and a suction on/off signal, and air feed flow and suction flow signals that are responsive to the amount of depression of each of the switches, these signals being sent to a signal processing circuit (33). The signal processing circuit (33) controls a air/water feed control valve 40 and a suction force control valve 50, so as to control air/water feed flow and suction flow, a flow display being made by an indicator (65) on the screen (63) of a TV monitor (35).

20 Claims, 8 Drawing Sheets

ENDOSCOPE APPARATUS

CROSS REFERENCE TO RELATED APPLICATIONS

This is a continuation-in-part of application Ser. No. 09/392,717, which was filed on Sep. 9, 1999, now abandoned, which is expressly incorporated by reference herein in its entirety.

BACKGROUND OF THE INVENTION

1. Field of the Invention

The present invention relates to an endoscope apparatus, and more particularly to an endoscope apparatus which notifies an operator of the flow amounts of such functions as air feed, water feed, and suction.

2. Discussion of Background

As control mechanisms for the functions of water feed, air feed, and suction in an endoscope apparatus for medical use, there exists the mechanical valve system, in which mechanical valves in an operating section are directly pressed, and a solenoid valve system, in which solenoid valves in a processor are controlled by means of signals from control switches in the operating section.

The mechanical valve system is the most commonly used control method, in which an operator directly operates mechanical valves so as to control air leakage, expansion and contraction of body cavities, and suction of residues. In this method, the air leakage condition is easily sensed both tactually and audibly by the operator, by means of the fingers and the ears, making it suitable for use by an operator who performs fine control of the amount of air feed and suction.

In an endoscope apparatus using the mechanical valve system, however, because of the complexity of the tubing, it is necessary when cleaning the apparatus to remove valves and wash and sterilize them separately, and additionally to grease sliding parts after cleaning. Additionally, because of intricate splitting of the tubing, brushing during cleaning requires a large amount of time. Maintenance, such as making connections the cleaning apparatus, is also complex and difficult. In addition, there is the problem of crushing a polyp when polyps are picked using suction.

While in the solenoid valve system, because of the simplicity of the tubing, brushing and connection to a cleaning apparatus are simplified, and it is possible to achieve more reliable cleaning and sterilization, in addition to there being no problem of the crushing of polyps.

Because of the on/off control used in the solenoid valve system of the past, this system was not suitable for use by an operator who performs control of the amount of air feed or suction. In recent years, however, there has been proposed an apparatus that enables arbitrary control of the amount of air feed and suction, and this problem is in the process of being resolved.

However, in an endoscope apparatus using the solenoid valve system that enables arbitrary control of the amount of air feed and suction, the control section that is provided in the endoscope apparatus main unit (processor) which controls the amount of air feed and suction in accordance with control signals from the scope operating section is at a position that is distant from the operator, making it impossible for the operator to obtain tactile or audible feedback to the senses thereof, the result being that the ease of operation of this type of endoscope apparatus does not reach that of a mechanical valve type of endoscope apparatus.

SUMMARY OF THE INVENTION

Accordingly, it is an object of the present invention to provide an endoscope apparatus that provides sensory feedback to an operator with regard the flow amount of air feed, water feed, suction, and the like, and which enables fine flow control.

In order to achieve the above-noted object, the present invention is an endoscope apparatus having an insertion part which is inserted into a body cavity, including at least one of a fluid feed channel and a suction channel, and having at least one of functions of feeding and sucking fluid through the channels, this endoscope apparatus having a flow controller that controls the flow amount of at least one of fed fluid and sucked fluid, and a display controller, which visually displays the flow amounts.

Another aspect of the invention is an endoscope apparatus having an insertion part which is inserted into a body cavity, including at least one of a fluid feed channel and a suction channel, and having at least one of functions of feeding and sucking fluid through the channels, the endoscope apparatus having a flow controller that controls the flow amount of at least one of fed fluid and sucked fluid, and a notification apparatus which makes notification of the flow amount by means of a sound.

According to the present invention, in addition to providing visual feedback of the amount of feed fluid and sucked fluid to an operator, enabling fine flow control, it is possible for nearby medical personnel other than the operator to know the amount of fluid flow, thereby achieving the effect of quickly discovering faulty operation or misoperation, and of usability in a medical education application.

BRIEF DESCRIPTION OF THE DRAWINGS

FIG. 7B is a bottom view of FIG. 7A, FIG. 7E is a bottom view of FIG. 7D, FIG. 7G is a side view of FIG. 7F, and FIG. 7H is a bottom view of FIG. 7F.

DETAILED DESCRIPTION OF THE PREFERRED EMBODIMENTS

Embodiments of the present invention are described in detail below, with reference to relevant accompanying drawings.

Figure 1:
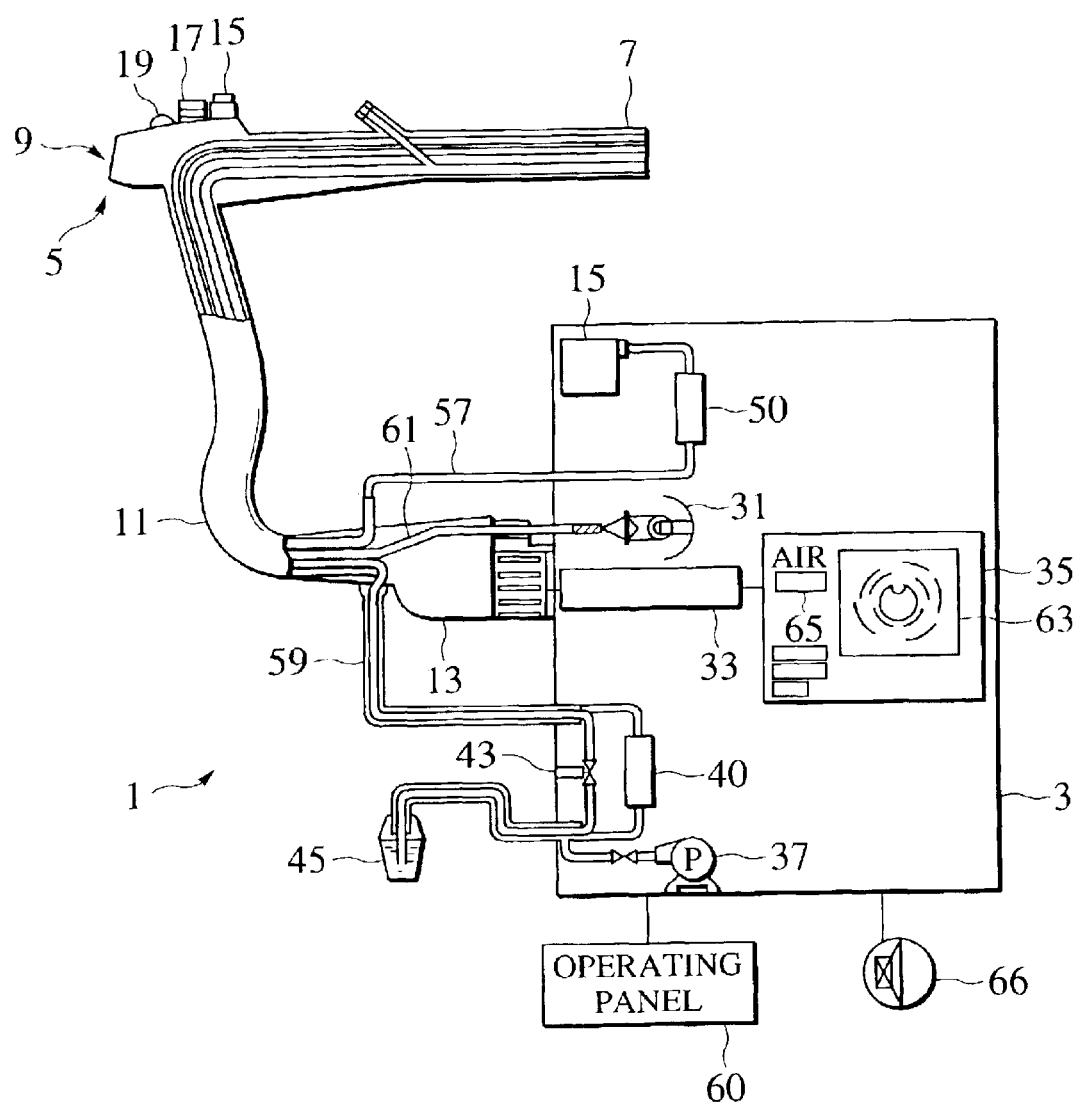
FIG. 1 is a drawing that shows the configuration of the first embodiment of an endoscope apparatus according to the present invention.

FIG. 1 shows the configuration of the first embodiment of an endoscope apparatus 1 according to the present invention, in which the endoscope apparatus 1 has an endoscope apparatus main unit 3 and an endoscope 5.

The endoscope 5 has an insertion part 7, the tip of which is fitted with an optical system and imaging element (not shown in the drawing), and which is inserted into a body cavity of the subject being examined, an operation section 9, which is continuous with the rear end of the insertion part 7, a universal cord 11 for the purpose of connecting the operating section 9 to the endoscope apparatus main unit 3, and a connector 13, which is provided on the end of the universal cord 11. The insertion part 7 includes a fluid feed channel through which water or air is fed into the body cavity and a suction channel through which fluid is sucked from the body cavity.

The operating section 9 has an air/water feed switch 15, which controls the feed of air and water, a suction switch 17, which controls suction, and a freeze switch (copy switch) 19, which temporarily freezes the image on a TV monitor 35 and issues an instruction to an image recording apparatus (not shown in the drawing) to record the image.

The endoscope apparatus main unit 3 has a light source, for the purpose of illuminating the inside of a body cavity of the subject under examination, a signal processing circuit 33, which processes a video signal and switching signals from the operating section, a TV monitor, which displays an image of the inside of a body cavity, an air/water feeding pump 37, which feeds air and water into the body cavity of the subject under examination, an air/water control valve 40, which controls the feed of air and water, an air/water feed switching valve 43, which control air/water feed, and a water feed bottle 45, which stores clean water to be fed. The air/water control valve 40 and the air/water feed switching valve 43 are provided in an air/water feeding line 59 which connects the air/water feed pump 37, water feed bottle 45 and the connector 13 of the endoscope 5.

The endoscope apparatus main unit 3 has a suction pump 51, and a suction force control valve 50, which is provided in the suction tubing path 57, which makes connection between the suction pump 51 and the connector 13.

The illumination light from the light source 31 is conducted to the tip of the insertion part 7 by a light guide 61, which passes through the operating section 9 and the insertion part 7, thereby illuminating the inside of a body cavity of the subject under examination. A video signal of an image acquired by the optical system and imaging element (not shown in the drawing) is input to the signal processing circuit 44 of the endoscope apparatus main unit 3, via the universal cord 11 and the connector 13, this signal undergoing prescribed processing and being displayed on the TV monitor 35 as an image 63 of a body cavity.

The endoscope apparatus main unit 3 is provided with an operating panel 60, from which it is possible to set whether or not flow display is to be made, enabling the flow display to be turned on and off, and to control an image on the TV monitor 35, volume and so on. By the operating panel 60, an display of the indicator 65 can be turned on and off, while keeping the display of the image 63 of a body cavity on the TV monitor 35. The display of the indicator 65 can be turned on and off separately from the display of the image 63 of a body cavity. An operator can select whether or not to display the indicator 65 on the TV monitor 35, while keeping a display of the image 63 of the body cavity. The endoscope apparatus main unit 3 is further provided with a speaker 66 which emanates a sound from a leakage nozzle which will be described later.

The amount of air flow instructed from the air/water feed switch 15, and the amount of suction flow instructed from the suction switch 17 are varied in strength in accordance with the amount that each of these switches is depressed. In the air/water feed mode, the amount of air feed or water feed is displayed by an indicator 65 on the TV monitor 35, and in the suction mode, the amount of suction is displayed in the same manner by the indicator 65 on the TV monitor 35.

Figure 2:
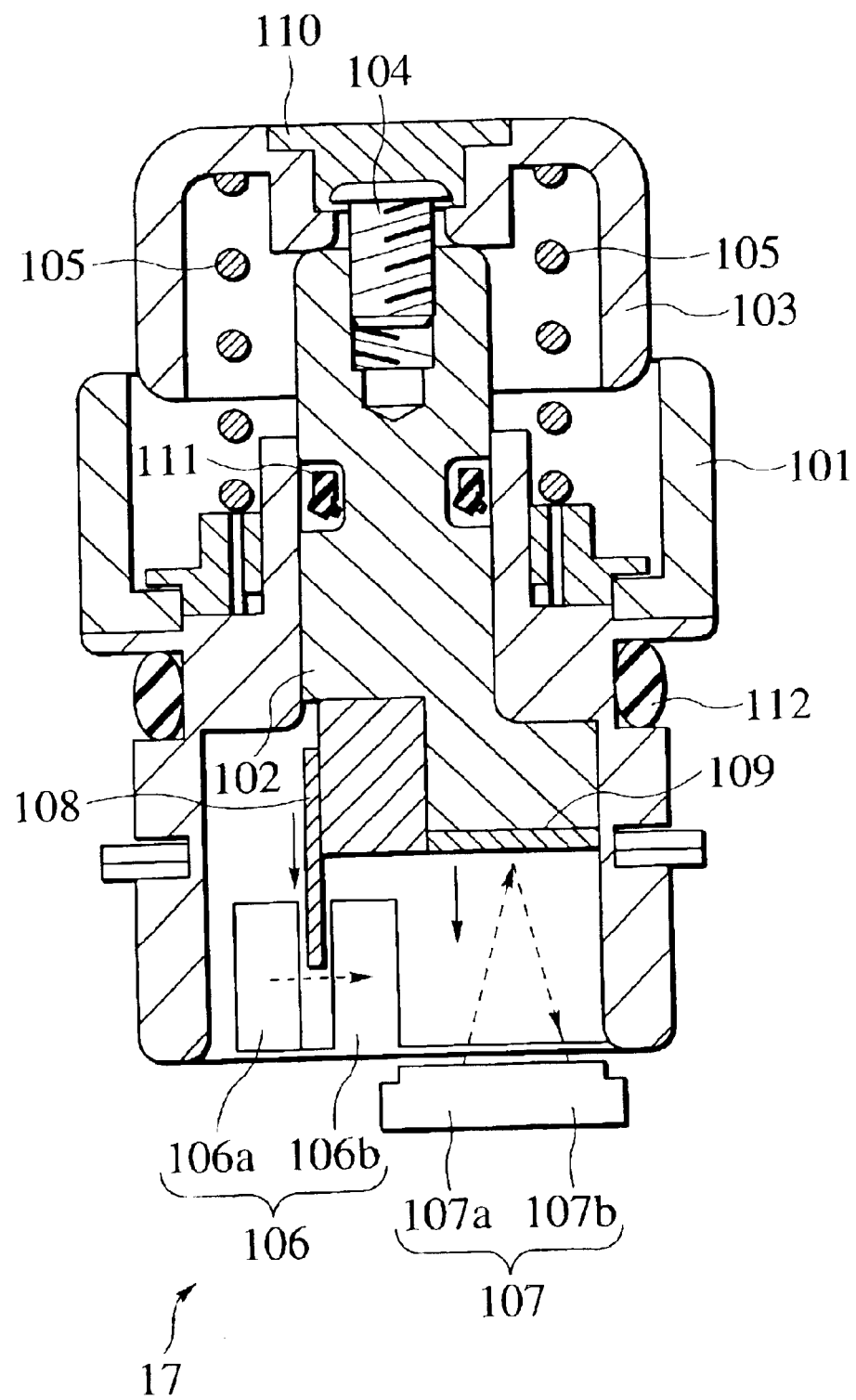
FIG. 2 is a longitudinal cross-section view that shows the construction of a suction switch applied to the present invention.

FIG. 2 shows a vertical cross-section view of the suction switch 17.

A feature of this suction switch 17 is that it has a transmission-type photo-interrupter 106, which performs on/off control of the suction, and a reflection-type photo-interrupter switch 107, which performs control of the amount of flow, in accordance with the amount of depression of the switch.

The suction switch 17 shown in FIG. 2 has a switch body 101, a cylinder 102 that serves as the main moving part, an operating button 103, a screw 104, which fastens the operating button 103 to the cylinder 102, a coil spring 105 that impels the operating button 103 upward against the switch body 101, a transmission-type photo-interrupter 106, which has a light-emitting section 106a and a light sensor 106b, a reflection-type photo-interrupter 107, which has a light-emitting section 107a and a light sensor 107b, a light baffle 108, which is fixed to the bottom part of the cylinder 102, a reflector plate 109, which is provided at the bottom part of the cylinder 102, a cap 110, which is buried in the top part of the operating button 103, a sealing ring 111, for the purpose of keeping airtight between the switch body 101 and the cylinder 102, and an O ring 112, for the purpose of keeping airtight between suction switch 17 and the case of the operating section (not shown in the drawing).

When the operating button 103 is depressed, the light baffle 108 that is provided at the bottom part of the cylinder 102 moves to block the light path between the light emitting section 106a and the light sensor 106b of the transmission-type photo-interrupter 106. As a result, there is a change in the signal level at the light sensor 106b, a suction-on signal being transmitted via the universal cord 11 and connector 12 to the signal processing circuit 33. Upon receiving this suction-on signal, the signal processing circuit 33 generates a signal that opens the suction force control valve 50, whereupon the suction force control valve opens, thereby turning the suction on.

From the point at which the suction is turned on, if the operating button 103 of the suction switch 17 is depressed further, the distance between the reflection-type photo-interrupter 107 and the reflector plate 109 shortens, in response to the amount of depression of the operating button 103, thereby causing the amount of light reaching the light sensor 107b from the light emitting section 107a to increase, a flow control signal responsive to this amount of light being sent from the light sensor 107b to the signal processing circuit 33.

Figure 3:
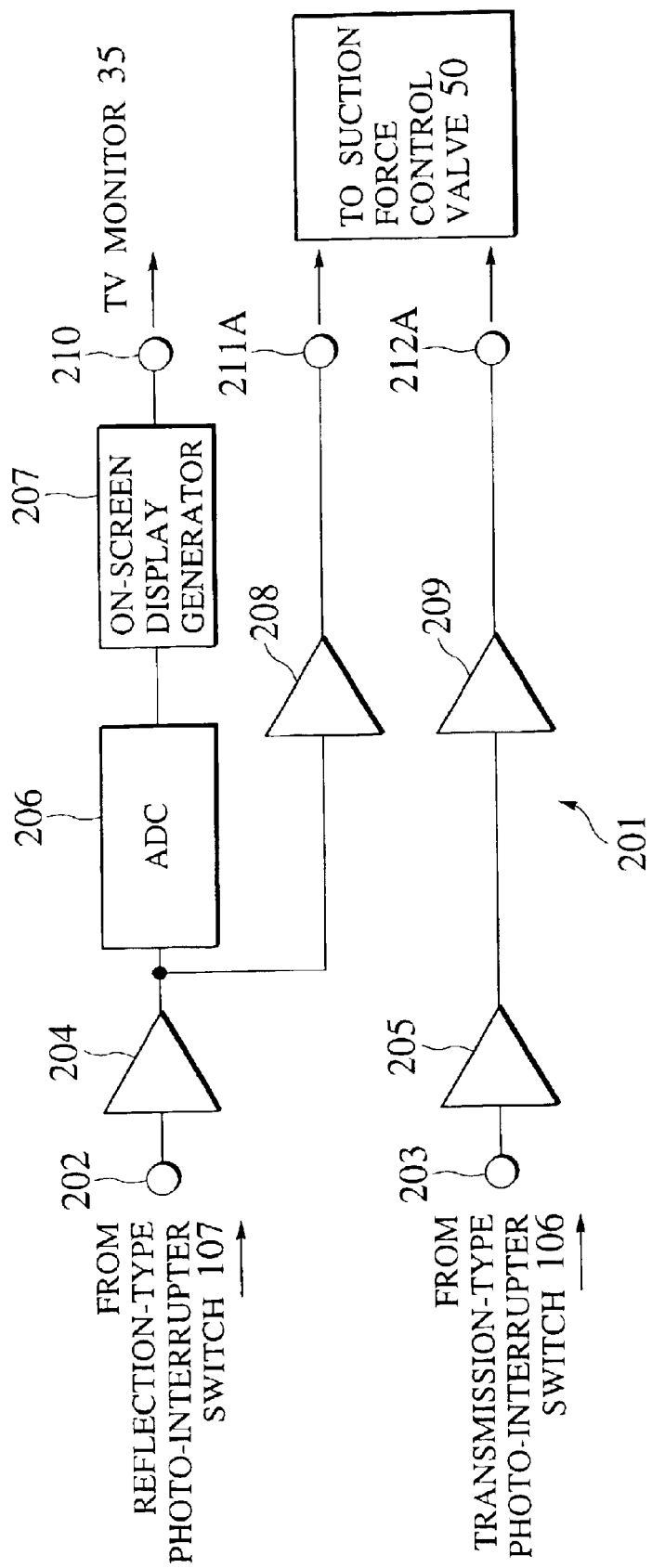
FIG. 3 is a block diagram of a flow control circuit for a suction force control valve in the first embodiment of the present invention.
Figure 4:
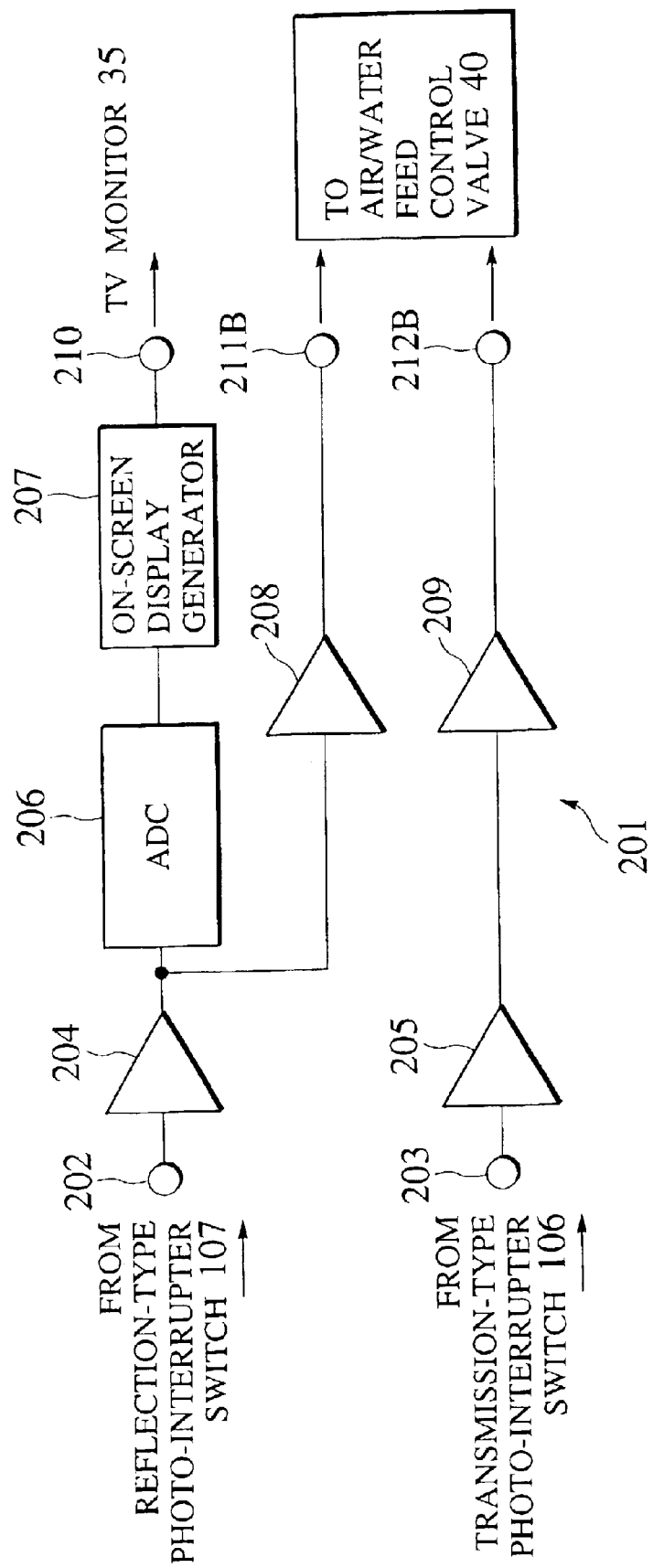
FIG. 4 is a block diagram of a flow control circuit for an air feed and water feed control valve in the first embodiment of the present invention.

FIG. 3 is a block diagram that shows a flow control circuit for a suction force control valve, this serving as the flow control part of the signal processing circuit 33, and FIG. 4 is a block diagram that shows a flow control circuit for an air/water feed control valve, this serving as the flow control part of the signal processing circuit 33.

The flow control circuit 201 shown in FIG. 3 has a flow control signal input terminal 202, at which is input a signal from the reflection-type photo-interrupter 107, an on/off signal input terminal 203, at which is input a signal from the transmission-type photo-interrupter 106, input amplifiers 204 and 205, an analog-to-digital converter (ADC) 206, an on-screen display generator 207, output amplifiers 208 and 209, a display output terminal 210, and suction force control valve control output terminals 211A and 212A.

The flow control circuit 201 includes a flow control display circuit, the flow control signal from the reflection-type photo-interrupter 107 that is input at the input terminal 202 being amplified by the amplifier 204, the amplified signal being then analog-to-digital converted by the ADC 206, the on-screen display generator 207 generating a display pattern that corresponds to the resulting digital quantity, this being output from the display output terminal 210 so as to display an indicator on the TV monitor 35.

Display by the indicator 65 can be, for example, a 10-segment bar display of level, with the display intensity of color of segments changing from the segment at one end toward the segment at other end of the bar display, in accordance with the amount of flow.

The signal that is amplified by the amplifier 204 is amplified by the output amplifier 208, the resulting signal being output at the suction force control valve control output terminal 211A for the purpose of controlling the amount of suction of the suction force control valve. The suction force control valve 50 has, for example, an electrical control apparatus such as a solenoid or motor, which controls the suction amount, in response to the drive signal that output from the suction force control valve output terminal 211A.

Because the configuration of the flow control circuit for an air/water feed control valve shown in FIG. 4 is the same as shown in FIG. 3, corresponding elements are shown with the same reference numerals, and the description thereof is not repeated herein. In this flow control circuit, the air or water flow amount is controlled in response to the drive signal that output from the air/water control valve output terminals 211B, 212B.

The air/water feed switch 15 has a construction that is substantially the same as that shown in FIG. 2, with the exception that the first transmission-type photo-interrupter (indicated by the reference numeral 106 in FIG. 2) that on/off controls the air feed has at its bottom part a second transmission-type photo-interrupter that on/off controls the water feed. The amount of air feed is controlled in response to the amount of depression of the switch. When the switch is depressed by the maximum amount, the light baffle blocks the path between the light emitting section and the light sensor of the second transmission-type photo-interrupter, so that a water feed signal is output. When this water feed signal is output, air feed stops and water feed starts.

The case of air/water feed has signal processing similar to the case of suction described above, with flow control of air/water being performed, the amount of flow being displayed on the indicator 65 of the TV monitor 35.

When both an air/water flow display and a suction flow display are provided, these can be selectively displayed by switching the indicator 65, or can be displayed on another separately provided indicator 65.

In the case in which selective display of air flow, water flow and suction is made on a single indicator 65, to clearly indicate which quantity is being displayed, it is preferable that markings be provided within the TV screen to indicate the displayed quantity. These markings can be, for example, the word AIR, WATER or SUCTION, or an abbreviation thereof. Another method of indicating this is to use color-coding of the display for air feed, water feed and suction. In addition, in a water feeding operation, because there are few cases in which a water flow amount is controlled, a water flow amount displaying can be omitted.

Additionally, the endoscope apparatus main unit 3 is provided with the operating panel 60, from which it is possible to set whether or not flow display is to be made, enabling the flow display to be turned on and off to suit the operators preference.

In the case in which the flow amount is notified to the operator by an audio signal, for example, a flow control signal that is amplified by the amplifier 204 of FIG. 3 controls the strength of an audible sound emanating from a speaker 66 by controlling the output level of an oscillator, or controls a voltage-controlled oscillator (VCO) so as to vary the frequency, volume, tone of a sound within the audible range to notify the operator. Yet another approach is to have this flow control signal cause an intermittent change in the pitch of the signal to notify the operator. The speaker 66 is preferably installed at a height that is near the height of the operator's ears, and can be, for example, provided in either the TV monitor or the scope operating section.

Even in the case in which the flow is indicated by an audio signal, it is preferable from the operating panel 60 to be able to set whether or not flow display is to be made, enabling the flow display to be turned on and off to suit the operators preference. The operating panel 60 can set to control so as to notify a flow amount to the operator by both indicator 65 and audio signal.

Figure 5:
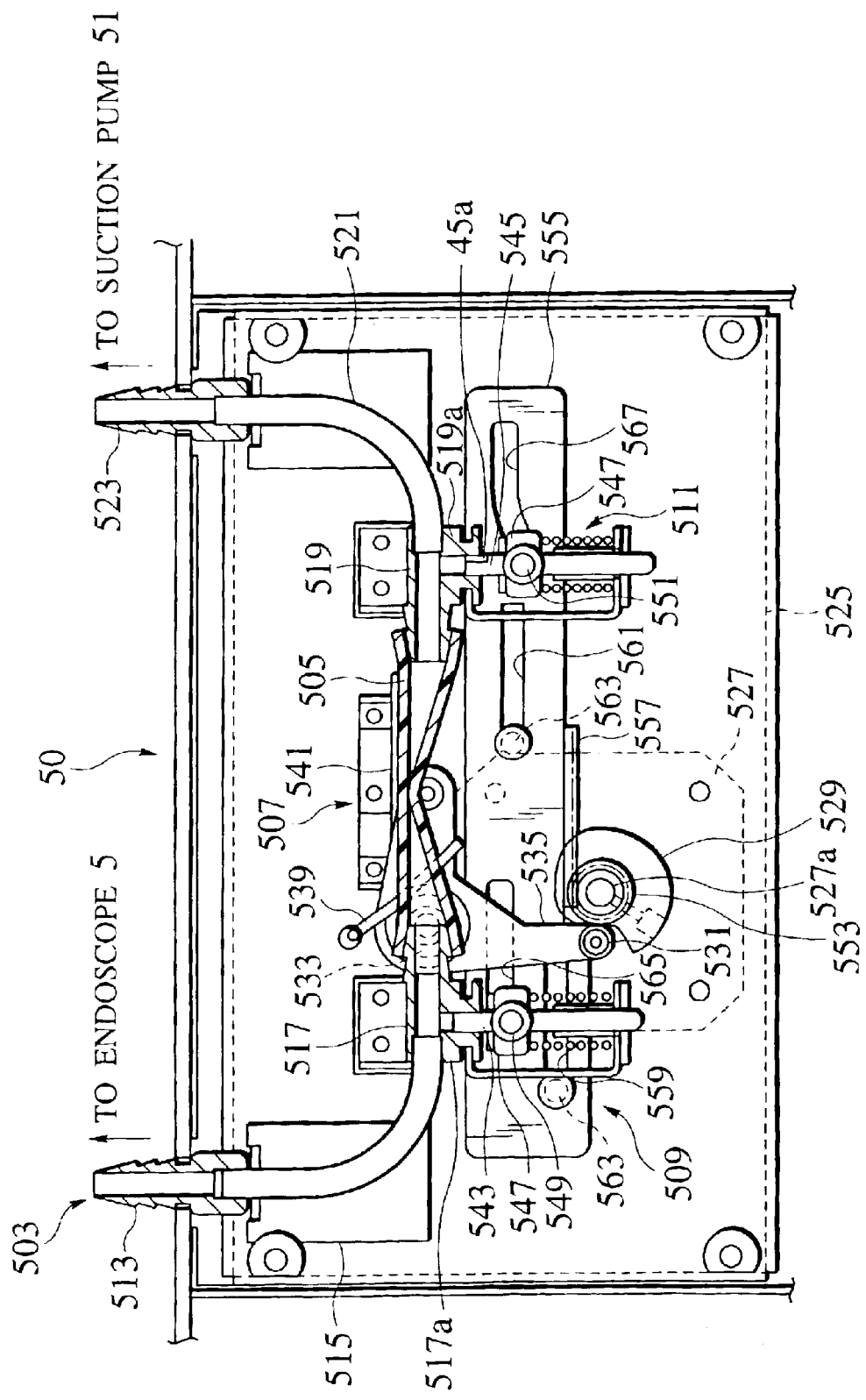
FIG. 5 is a drawing that shows the configuration of a suction force control valve in the first embodiment of the present invention.

FIG. 5 shows the configuration of a suction force control valve 50. This suction force control valve 50 has a suction tubing path 503 which makes a connection between the suction pump 51 and the endoscope 5, a variable pinch valve 507, which continuously varies the cross-sectional area of a flexible tube 505 that is provided in the suction tubing path 503, a leakage valve 509, which is provided on the upstream side (scope insertion part side) of the variable pinch valve 507, and a leakage valve 511 that is provided on the downstream side (suction pump side) of the variable pinch valve 507. The amount of outside air leakage in the leakage valves 509 and 511 is linked to the change in the opening of the variable pinch valve 507.

The suction tubing path 503 has a hose end 513 and a hose end 523, between which are connected in sequence a bent tube 515, a divided tube 517, the flexible tube 505, a divided tube 519, and a bent tube 521, the hose end 523 being connected to the suction pump 51.

The divided tubes 517 and 519 are provided with the leakage valves 509 and 511, respectively, enabling leakage of outside air.

The variable pinch valve 507 is formed by a motor 527 which is a source of motive power that is fixed to the rear surface of the frame 525, a cam 529 that is fixed to the shaft 527a of the motor 527, a L-shaped lever 535, a roller 531 provided on one end of which makes contact with the cam 529, the rotation of the cam 529 causing the L-shaped lever 535 to undulate about the lever shaft 533, a pin 537 that is provided on the other end of the lever 535, a spring 539 that impels the lever 535 in the counterclockwise direction, so that it presses up against the cam 529, and a plate 541 that is fixed to the frame 525 at a position such the flexible tube 505 is held between it and the opposing pin 537.

When the cam 529 swings in the counterclockwise direction from the position at which the variable pinch valve 507 is closed as shown in FIG. 5, the roller 531 is gradually pressed to the left, thereby causing the lever 535 to swing in the clockwise direction about the lever shaft 533, this resulting in the movement of the pin 537 downward as shown in drawing, thereby opening up the distance between it and the plate 541 so as to reduce the amount of restriction of the flexible tube 505 by the plate 541 and the pin 537, causing an increase in the cross-sectional area of the flexible tube 505, thereby starting the suction.

In contrast to the above operation, when the suction is to be stopped, the motor 527 is driven in reverse, so that the cam 529 is caused to rotate in the clockwise direction. This rotation causes the roller 531 to return gradually to the right side, causing the lever 535 to swing in the counterclockwise direction about the lever shaft 533, so that the pin 537 moves upward as shown in the drawing, so that its distance from the plate 541 is reduced, the result being an increase in the amount of restriction of the flexible tube 505 by the plate 541 and the pin 537, thereby gradually decreasing the cross-sectional area of the flexible tube 505, until ultimately the suction is stopped when the flexible tube 505 is completely restricted.

The leakage valves 509 and 511 are provided on the divided tubes 517 and 519, respectively. The cylinder parts 517 and 519a that divide off downward in the drawing from the divided tubes 517 and 519 are each fitted to cylindrical pistons 543 and 545, pins 549 and 551 being fixed, via a bracket 547 to these pistons 543 and 545. In response to the up and down movement of the pins 549 and 551, the respective pistons 543 and 545 move up and down, so as to cause leakage or the stoppage of leakage of outside air by the respective leakage valves 509 and 511.

The operation of the leakage valves 509 and 511 differs as follows. Because the end part of the piston 543 of the leakage valve 509 on the endoscope side is merely chamfered, the control made in accordance with the position of the piston 543 with respect to the cylinder 517a is substantially on/off control. The end part of the piston 545 on the suction pump side, however, is provided with a cutout 545a, so that the amount of leakage obtained is responsive to the amount that the piston 545 is pulled out from the cylinder 519a.

The mechanism that links the opening and closing of the leakage valves 509 and 511 or the amount of leakage to the opening and closing of the variable pinch valve 507 is as follows.

The shaft 527a of the motor 527 is provided with a pinion gear 553 that is fixed to the bottom part of the cam 529, so that it rotates with rotation of the cam 529. The end part of the front of a cam plate 555 that is disposed on the upper surface of the frame 525 and parallel thereto is provided with a rack gear 557 that meshes with the pinion gear 553. The cam plate 557 is provided with elongated holes 559 and 561, which extend to the left and right so as to limit the left-to-right sliding thereof, a pin 563 that stands erect from the frame 525 being inserted through the elongated holes 559 and 561. By virtue of this arrangement, the cam plate 555 slides to the right with a clockwise rotation of the pinion gear 553, and slides to the left with a counterclockwise rotation of the pinion gear 553.

The cam plate 555 is provided with a cam groove 565 that has an inclined part that is inclined with respect to the left and right directions, a pin 549 being inserted into the cam groove 565, so that with a left-to-right movement of the cam groove 565, the pin 549 moves up and down. The pin 549 is fixed to the piston 543 of the leakage valve 509, via a bracket 547, as noted above. By means of this arrangement, when the cam plate 555 is driven left and right by the pinion gear 553, the pin 549 that slides in the cam groove 565 moves up and down, resulting in the piston 543 moving into and out of the cylinder 517a of the divided tube 517, thereby opening and closing the leakage valve 509.

In the same manner, the cam plate 555 is provided with a cam groove 567 that has a has an inclined part that is inclined with respect to the left and right directions, a pin 551 being inserted into the cam groove 567, so that with a left-to-right movement of the cam groove 567, the pin 551 moves up and down. The pin 551 is fixed to the piston 545 of the leakage valve 511, via the bracket 547. By means of this arrangement, when the cam plate 555 is driven left and right by the pinion gear 553, the leakage valve 551 is opened and closed and the amount of leakage is changed, in the same manner as described above.

That is, during the time in which the variable pinch valve 507 is closed, the leakage valves 509 and 511 leak outside air. As the cam 529 and the pinion gear 553 rotate in the counterclockwise direction, the variable pinch valve 507 gradually opens, and the leakage valve 509 closes, so that the amount of leakage of the leakage valve 511 becomes small, this feature being convenient, for example, in using the suction force of the suction pump 51 to retrieve by suction an object from the tips of a pair of forceps at the open end of the endoscope insertion part.

At the maximum rotation position of the cam 529, the opening of the variable pinch valve 507 is maximum, and the amount of leakage of the leakage valve 511 is zero.

Figure 6:
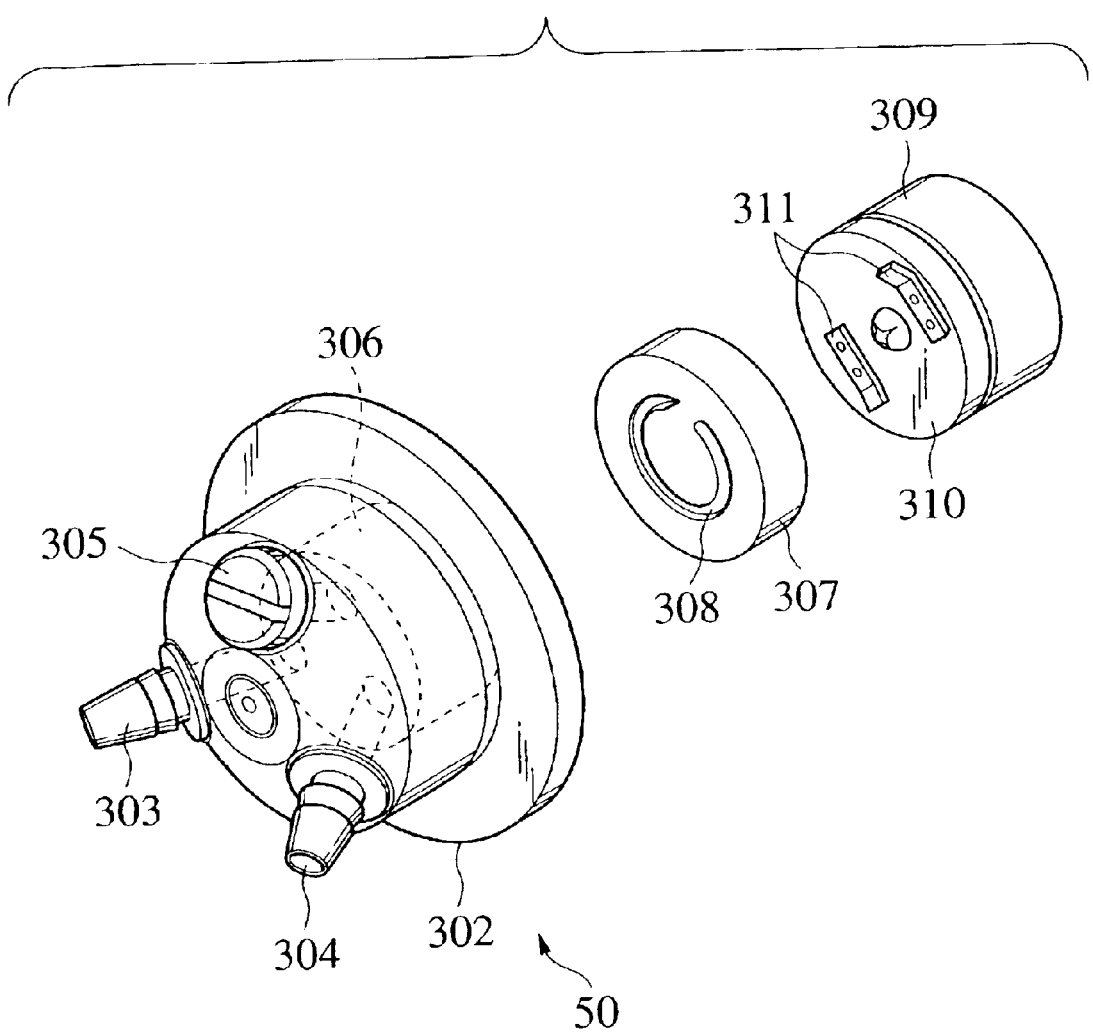
FIG. 6 is an exploded perspective view that shows the construction of a suction force control valve in the second embodiment of the present invention.

FIG. 6 is an exploded perspective view showing the main part of the second embodiment of an endoscope apparatus according to the present invention, this drawing showing the structure of a suction valve that is provided at the front panel of the endoscope apparatus main unit. In this embodiment, the leakage sound of an electrically controlled suction force control valve can be heard directly by an operator.

In FIG. 6, the suction force control valve 50 is driven by a motor 309.

In FIG. 6, the rear surface of the valve case 302 is provided with a depression 306 having the shape of a short cylinder, the front surface being provided with a suction fitting for connection with a suction device (not shown in the drawing), an endoscope fitting 304 for connection with an endoscope (not shown in the drawing), and a leakage nozzle 305. The suction fitting 303, the endoscope fitting 304, and the leakage nozzle 305 are communicate with the depression 306 at the rear of the valve case 302.

The depression 306 has fitted to it a rotary valve 307 having the shape of a short cylinder, the front surface of this rotary valve 307 being provided with a C-shaped groove 308, one end of that narrows gradually. The rear surface of the rotary valve 307 is provided with depressions (not shown in the drawing) at two locations, a joining plate 310 having two joining tabs 311 in corresponding positions pressing up against the rear of the rotary valve 307. The joining plate 310 can be driven by the motor 309 either forward or in reverse.

That is, the rotation of the motor 309 causes the positions of the groove 308 of the rotary valve 307 to rotate, so as to perform on/off control of the communication established by the groove 308 between the suction fitting 303 and the endoscope fitting 304, while varying the cross-sectional area of the leakage path with respect to the leakage nozzle 305, so that the rotation of the motor performs both on/off control of the suction and flow control of the suction.

The leakage nozzle 305 additionally generates a suction sound that is continuously responsive to changes in the amount of leakage. By means of the intensity of the suction sound generated by the leakage nozzle 305, an operator can continuously sense whether there is a lit or little leakage, that is, whether there is a little or a lot of suction. In addition, it is possible to provide a microphone in proximity to the leakage nozzle, to convert the leakage sound to an electrical signal which, after amplification, can be used to drive the speaker 66 so as to emanate a sound.

FIG. 7A through FIG. 7H are cross-section views and bottom views and side view that show various leakage nozzles in detail.

Figure 7A:
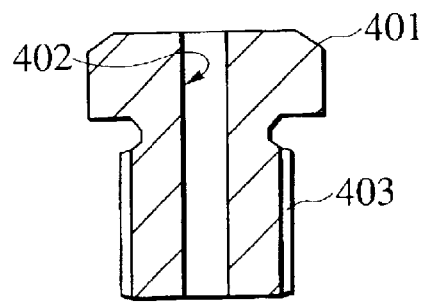
FIG. 7A through FIG. 7H are cross-section, bottom and side views that show the construction of a leakage nozzle used in the suction force control valve according to the second embodiment of the present invention.
Figure 7B:
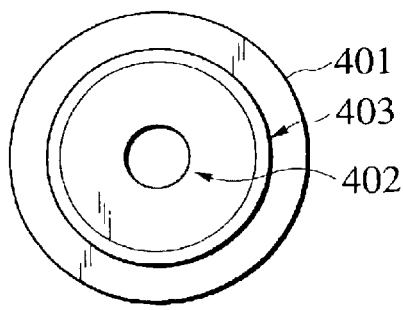

The leakage nozzle 401 shown in FIGS. 7A and 7B is an example in which there is through hole 402 having a circular cross section. The outer periphery is provided with a male threaded part 403 for the purpose of mounting the nozzle to the valve case 302 shown in FIG. 6.

Figure 7C:
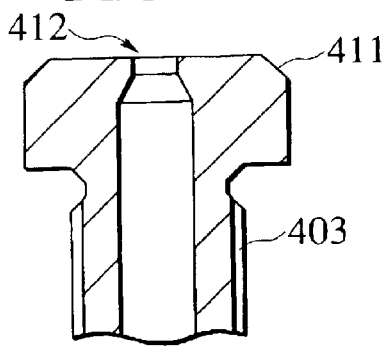
Figure 7D:
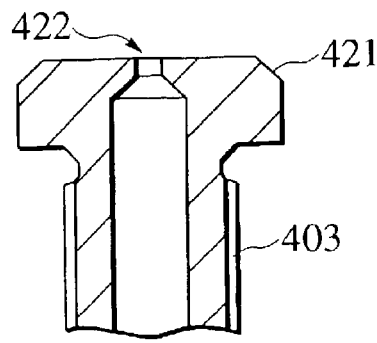
Figure 7E:
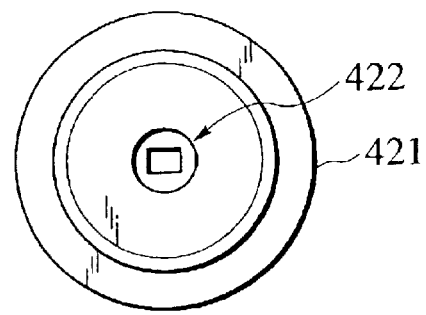
Figure 7F:
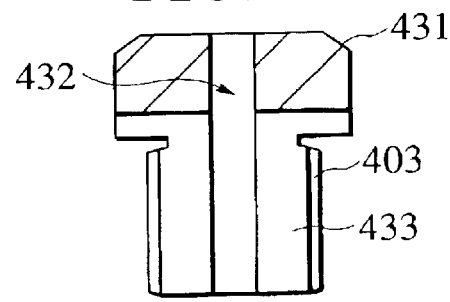
Figure 7G:
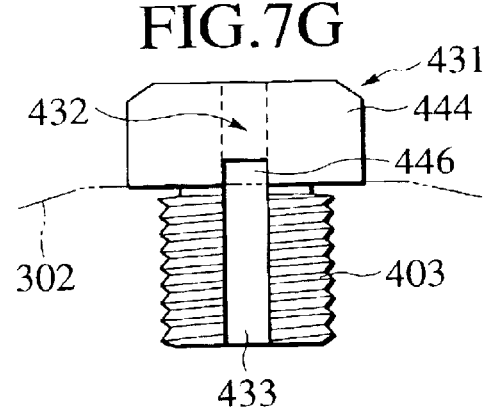
Figure 7H:
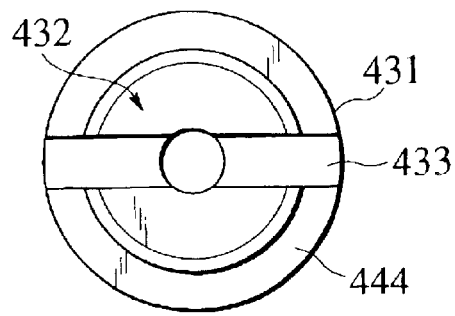

Because the straight through hole 402 does not provide good sound generation with sufficient volume, it is preferable to use a leakage valve 411, shown in FIG. 7C, having a narrowly restricted through hole, a leakage valve 421, shown in FIG. 7D and FIG. 7E, which has a through hole 422, the end of which has a rectangle cross section, or a leakage valve 431, shown in FIG. 7F, FIG. 7G and FIG. 7H, having a through hole 432 and a slit formed at the lower portion along with the through hole 432. When this leakage valve 431 is mounted on the valve case which is shown in a phantom line, an opening 446 formed between the valve case 302 and the valve head 444, and a leakage sound is generated by the opening 446.

Figure 8A:
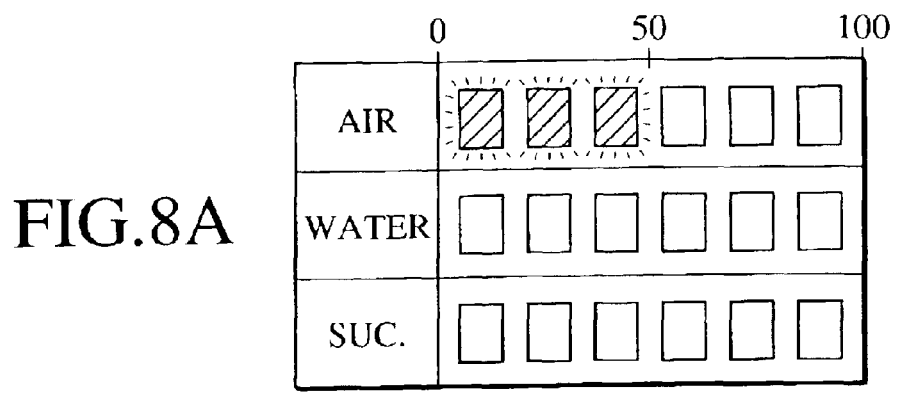
FIG. 8A through FIG. 8D are drawings that show modifications of the indicator in the first and second embodiments.
Figure 8B:
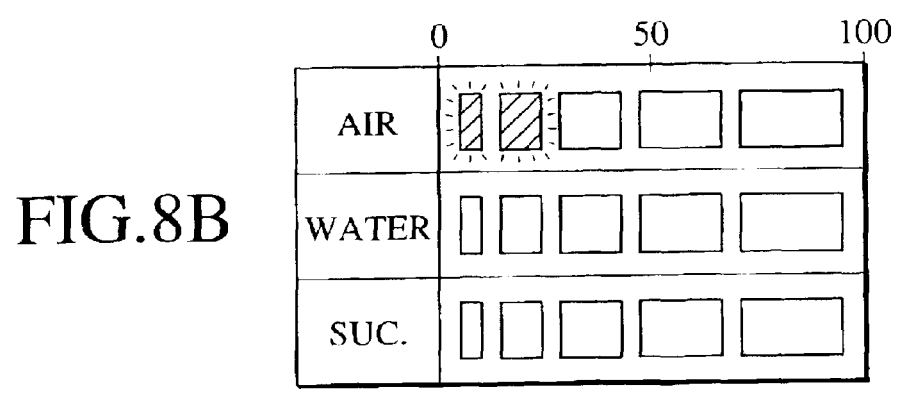

FIG. 8A, FIG. 8B, FIG. 8C, FIG. 8D show modifications of the indicator of the first and second embodiments. In FIG. 8A, "AIR", "WATER", "SUC" are indicated in parallel, and one of these is selected to indicate a flow amount by the number of the segments. The segments are displayed on TV monitor 35 in response with the flow amount or lighted by a light emitting diode (LED) and so on which is arranged separately from the TV monitor 35. In FIG 8B, the flow amount is indicated non-linearly. Namely, the segments have different lengths which are lengthened in accordance with the flow amount. In this case, the indicator 65 may be linked with the speaker 66 so as to notify an operator of the flow amount with both indicator 65 and speaker 66.

Figure 8C:
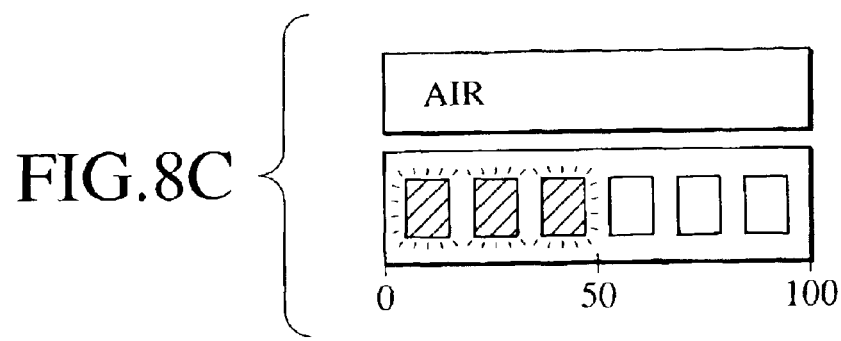
Figure 8D:
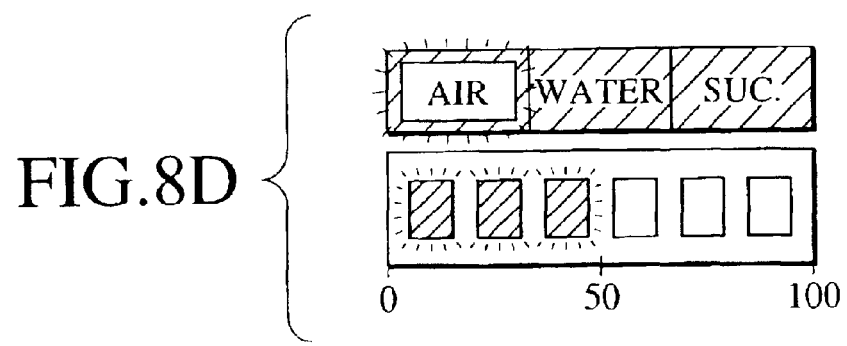

In FIG. 8C, one of "AIR", "WATER" and "SUC" is selected by the operating panel 60 to be indicated. The flow amount is indicated with the number of the segments, and each segment is lighted by the LED and so on in accordance with the flow amount. In FIG. 8D, one of "AIR", "WATER" and "SUC" is selected by the operating panel 60 to be lighted by the LED and so on.

In addition, because there is few case in which the water flow amount is controlled, the water flow amount displaying may be omitted.

What is claimed as new and desired to be secured by Letters Patent of the United States is:

1. An endoscope apparatus having an insertion part inserted into a body cavity, the insertion part including at least one of a fluid feed channel and a suction channel, the endoscope apparatus comprising:
    a flow controller configured to control a flow amount of at least one of fed fluid through the feed channel and sucked fluid through the suction channel;
    a display controller configured to display an image of the body cavity on an observation monitor;
    a switch configured to generate a signal in response to an amount of depression of the switch, wherein the flow controller uses the signal from the switch to control fluid flow; and
    a notification apparatus configured to generate a sound notification of the flow amount.

2. An endoscope apparatus according to claim 1, wherein the switch comprises a reflection-type photo-interrupter which performs control of an amount of flow in accordance with an amount of operation of the switch.

3. An endoscope apparatus according to claim 1, wherein the switch performs on/off control of the fluid flow.

4. An endoscope apparatus according to claim 3, wherein the switch comprises a transmission-type photo-interrupter which performs on/off control of the fluid flow.

5. An endoscope apparatus according to claim 1, wherein the notification apparatus varies at least one of tone, pitch, volume and pulse of sound in response to the flow amount.

6. An endoscope apparatus according to claim 1, wherein the notification apparatus comprising a speaker configured to emanate a sound that is responsive to the flow amount.

7. An endoscope apparatus according to claim 1, further comprising a control valve configured to control the flow amount in accordance with a signal from the flow controller, wherein the notification apparatus comprises a leakage nozzle that is provided on the control valve, the leakage nozzle being configured to generate a sound that is responsive to the flow amount.

8. An endoscope apparatus according to claim 7, wherein the leakage nozzle is provided with a through hole having a circular cross section for generating said sound.

9. An endoscope apparatus according to claim 7, wherein the leakage nozzle is provided with a through hole provided with an exit having a smaller diameter than the through hole.

10. An endoscope apparatus according to claim 7, wherein the leakage nozzle is provided with a through hole provided with an exit having a rectangular cross section.

11. An endoscope apparatus according to claim 7, wherein the leakage nozzle is provided with a slit which forms an opening for generating said sound when the leakage nozzle is mounted.

12. An endoscope apparatus according to claim 1, wherein the flow controller is configured to control the flow amount of the fed fluid through the feed channel.

13. An endoscope apparatus according to claim 1, wherein the flow controller is configured to control the flow amount of the sucked fluid through the suction channel.

14. An endoscope apparatus according to claim 13, wherein the flow controller is further configured to control the flow amount of the fed fluid through the feed channel.

15. An endoscope apparatus according to claim 1, further comprising an operation section mechanically coupled to said insertion part.

16. An endoscope apparatus according to claim 15, wherein said switch is mounted on said operation section.

17. An endoscope apparatus according to claim 16, wherein said operation section is continuous with a rear end of said insertion part.

18. An endoscope apparatus according to claim 1, wherein the notification apparatus comprises a leakage nozzle configured to generate a sound that is responsive to the flow amount.

19. An endoscope apparatus according to claim 18, wherein the notification apparatus further comprises a microphone configured to convert said sound to an electrical signal.

20. An endoscope apparatus according to claim 19, wherein the notification apparatus further comprises a speaker configured to be driven by said electrical signal from said microphone.

* * * * *